US009233132B2

(12) United States Patent
Zhang et al.

(10) Patent No.: US 9,233,132 B2
(45) Date of Patent: Jan. 12, 2016

(54) LUNG CANCER THERAPY USING AN ENGINEERED RESPIRATORY SYNCYTIAL VIRUS

(71) Applicants: Weidong Zhang, Tampa, FL (US); Lixian Jiang, Wesley Chapel, FL (US); Calvin Cao, Tampa, FL (US)

(72) Inventors: Weidong Zhang, Tampa, FL (US); Lixian Jiang, Wesley Chapel, FL (US); Calvin Cao, Tampa, FL (US)

( * ) Notice: Subject to any disclaimer, the term of this patent is extended or adjusted under 35 U.S.C. 154(b) by 0 days.

(21) Appl. No.: 13/790,278

(22) Filed: Mar. 8, 2013

(65) Prior Publication Data

US 2013/0251680 A1 Sep. 26, 2013

Related U.S. Application Data

(60) Division of application No. 12/925,886, filed on Nov. 2, 2010, now abandoned, and a continuation-in-part of application No. 12/800,585, filed on May 18, 2010, now Pat. No. 8,597,637.

(60) Provisional application No. 61/398,236, filed on Jun. 22, 2010.

(51) Int. Cl.

| | |
|---|---|
| ***A61K 35/76*** | (2015.01) |
| ***A61K 35/768*** | (2015.01) |
| ***C12N 7/00*** | (2006.01) |

(52) U.S. Cl.

CPC ................ *A61K 35/768* (2013.01); *C12N 7/00* (2013.01); *C12N 2760/18532* (2013.01); *C12N 2760/18543* (2013.01)

(58) Field of Classification Search

None

See application file for complete search history.

(56) References Cited

U.S. PATENT DOCUMENTS

| | | | | |
|---|---|---|---|---|
| 6,986,881 | B1 | 1/2006 | Livingston et al. | |
| 7,709,007 | B2 | 5/2010 | Murphy et al. | |
| 8,597,637 | B1 * | 12/2013 | Zhang et al. | 424/93.2 |
| 2004/0109877 | A1 | 6/2004 | Palese et al. | |
| 2010/0303839 | A1 | 12/2010 | Bose et al. | |

OTHER PUBLICATIONS

Shayakhmetov, et al. (2004) "Analysis of Adenovirus Sequestration in the Liver, Transduction of Hepatic Cells, and Innate Toxicity after Injection of Fiber-Modified Vectors", Journal of Virology, 78(10): 5368-81.*

Liu, et al. (2009) "Combined IFN-gamma-endostatin gene therapy and radiotherapy attenuates primary breast tumor growth and lung metastases via enhanced CTL and NK cell activation and attenuated tumor angiogenesis in a murine model", Annals of Surgical Oncology, 16(5): 1403-11.*

Krilov, et al. (1993) "Inactivation of respiratory syncytial virus by detergents and disinfectants", The pediatric infectious disease journal, 12(7): 582-84 (Abstract Only).*

Gisela Enders (1996) "Chapter 59: Paramyxoviruses", Medical Microbiology, 4th Ed., S. Baron, Editor, Published by the University of Texas Medical Branch at Galveston, Galveston, TX., 18 pages long.*

Muster et al. (2004) Int. J. Cancer 110, 15-21.

Restifo et al. (1998) Virology 249, 89-97.

Shayakhmetov et al. (2004) J. Virology 78, 5368-81.

Spann et al. (2004) J. Virology 78, 4363-69.

Munir et al. (2008) J. Virology 82, 8780-96.

Hao et al. (2007) Molecular Cancer Therapeutics 6, 2220-29.

Mohapatra et al. (2007) Molecular Cancer Research 5, 141-151.

Everts et al. (2005) Cancer Gene Therapy, 12, 141-161.

Chattopadhyay et al. (2004) Virus Research, 99, 139-145.

Smallwood et al. (2002) Virology, 304, 135-145.

Tomasinsig et al. (2005) Current Protein and Peptide Science, 6, 23-34.

Skolnick et al. (2000) Trends in Biotech, 18, 34-39.

J. Denry Sato and Mikio Kan (1998) Current Protocols in Cell Biology, "Media for culture of mammalian cells," pp. 1.2.1 to 1.2.15.

* cited by examiner

*Primary Examiner* — Robert M Kelly

(57) ABSTRACT

The invention discloses an engineered oncolytic respiratory syncytial virus (RSV), NS1 gene deficient RSV, and its usage to treat lung cancer by killing cancer cells with in vitro and in vivo evidences.

3 Claims, 13 Drawing Sheets

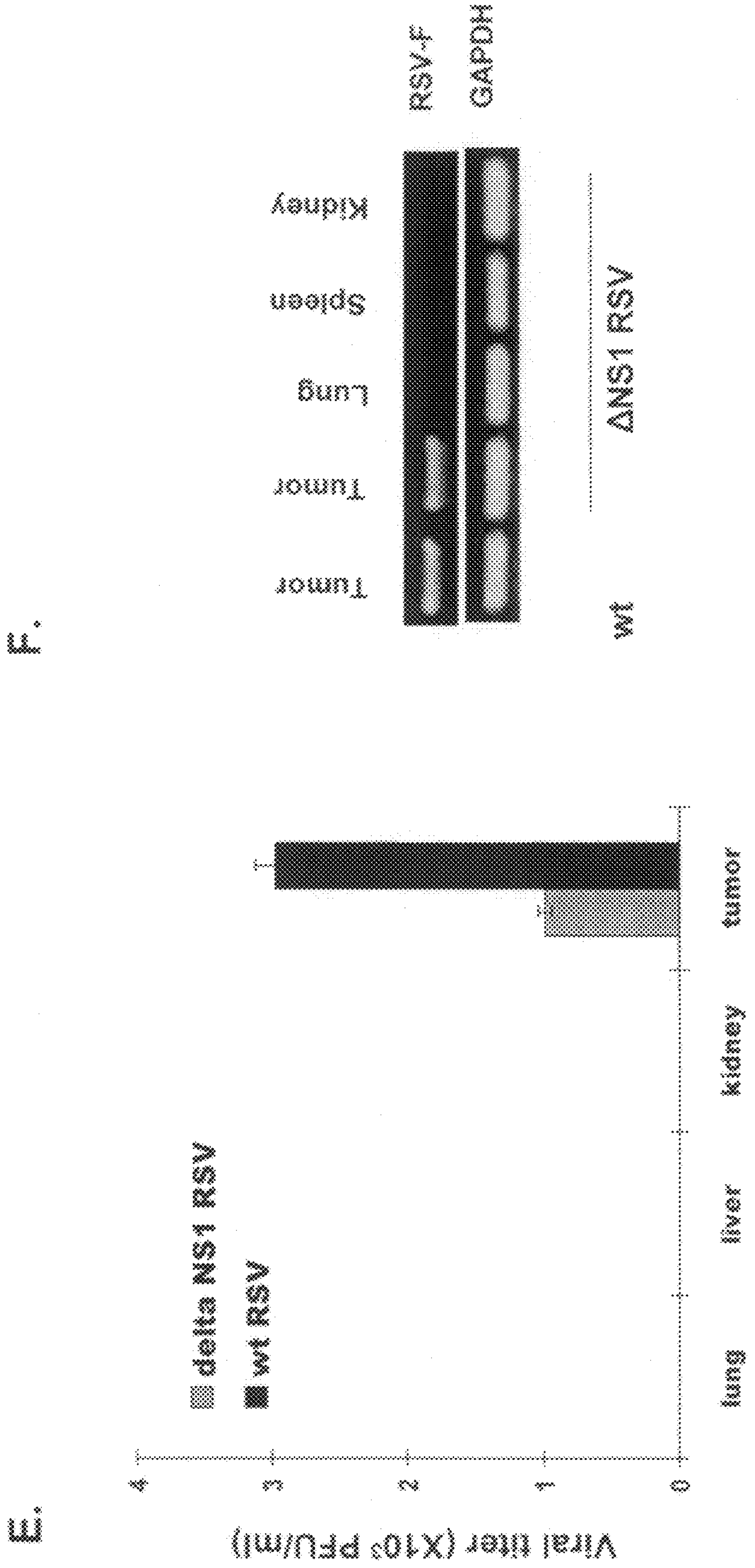
Figure 2E, F

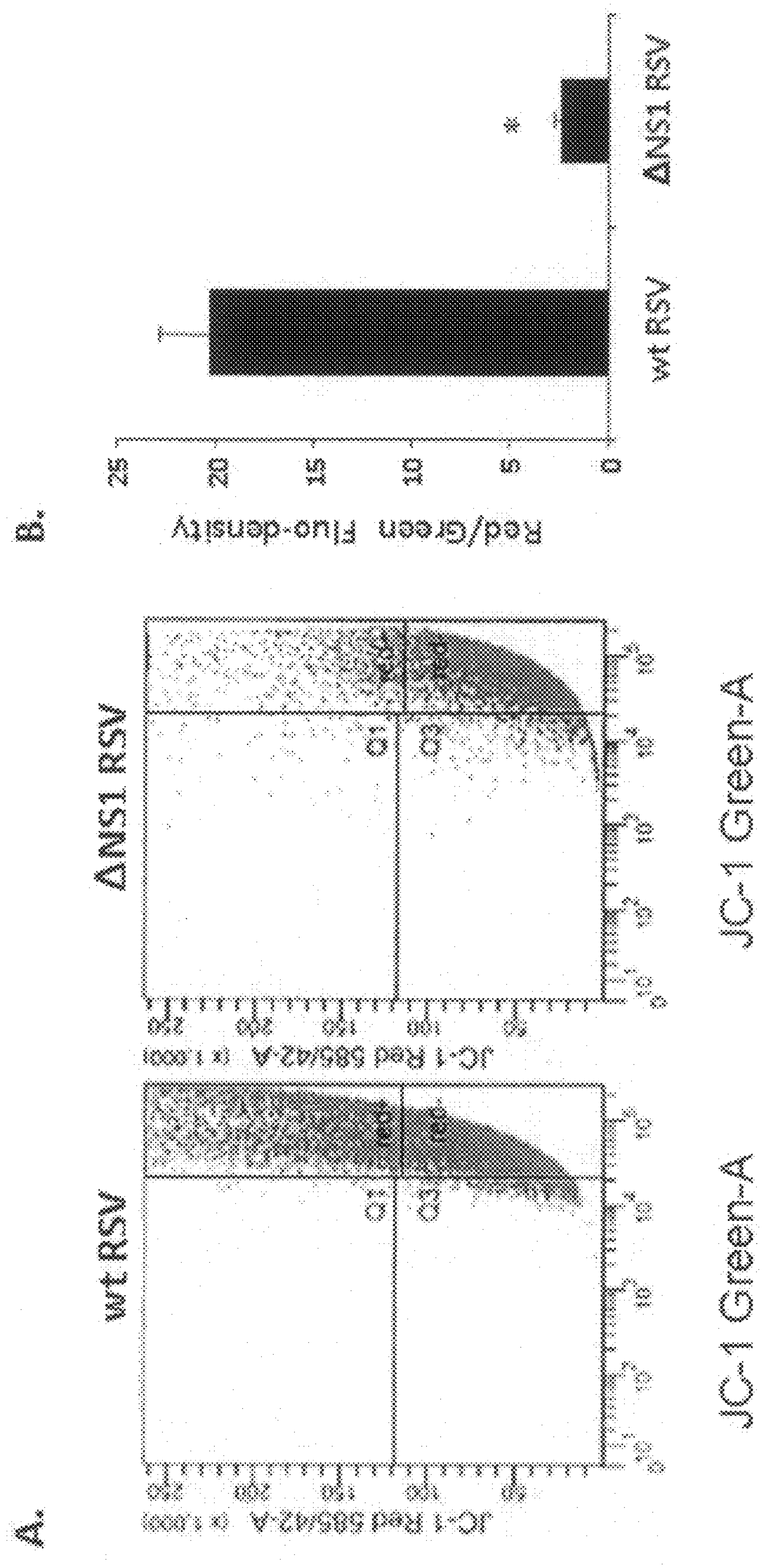
Figure 5A, B

LUNG CANCER THERAPY USING AN ENGINEERED RESPIRATORY SYNCYTIAL VIRUS

CROSS-REFERENCE TO RELATED APPLICATIONS

This application claims benefit, as a divisional, of U.S. application Ser. No. 12/925,886, filed Nov. 2, 2010, which claims priority to U.S. non-provisional application Ser. No. 12/800,585, filed on May 18, 2010, and U.S. provisional Application No. 61/398,236, filed on Jun. 22, 2010, the disclosures of which are incorporated herein in their entirety by reference.

FIELD OF THE INVENTION

The invention is within the scope of oncolytic virotherapy. We engineered respiratory syncytial virus (RSV) by deleting NS1 gene, and found that the NS1 gene deficient-RSV (ΔNS1 RSV) can kill lung cancer cells, but not normal human cells.

BACKGROUND OF THE INVENTION

Lung Cancer: Treatment and Survival.

Lung cancers are divided by histopathology into small cell lung cancers (~15%) and NSCLC (~85%) [1]. In 2009, 219,440 new cases are expected and 159,390 persons are projected to die from lung cancer in the United States [2]. Prevailing treatments have only limited success in lung cancer, particularly NSCLC, which becomes resistant to the drugs used for chemotherapy.

Radiotherapy, alone or in combination with surgery or chemotherapy, is useful in the management of NSCLC [3]. However, tumor radio-resistance, including intrinsic radio-resistance before treatments and acquired radio-resistance during radiotherapy, makes radiotherapy problematic for NSCLC [4]. There is no effective treatment available for advanced or metastatic NSCLC [5]. The global increase in lung cancer, together with its poor survival rate and resistance to classical chemotherapy, underscores the need for development of novel therapeutic strategies.

Oncolytic Virotherapy.

Oncolytic virotherapy is a novel strategy using viruses, either naturally occurring or genetically modified, to selectively target and destroy tumor cells while leaving surrounding non-malignant cells unharmed [6]. Our preliminary data show that ΔNS1 RSV replicates to a high titer in lung tumor cells, compared to the normal WI-38 diploid lung cells (FIG. 2B), and ΔNS1 RSV, not wt RSV, specifically kills lung cancer cells, but not normal WI-38 or NHBE cells (FIGS. 2A and 4A and Table 1). NS1 protein functions as an anti-apoptotic factor (FIG. 4A, B) and deletion of NS1 restores the apoptotic pathway in tumor cells.

TABLE 1

ΔNS1 RSV preferentially kills human lung cancer cells.

| Cells | Virus (MOI = 10) ΔNS1 RSV CPE (24 h post-infection) | Virus (MOI = 10) wt RSV CPE (24 h post-infection) |
|---|---|---|
| WI-38 cells (Human normal embryonic lung fibrolast) | – | – |
| NHBE cells (Normal human bronchial epithelial) | – | – |
| H157 cells (erlotinib-resistant) | ++++ | – |
| H480 cells (erlotinib- and dasatinib-resistant) | ++++ | – |
| H1299 cells (erlotinib-resistant and p53–/–) | ++++ | – |
| H441 cells (erlotinib- and dasatinib-resistant) | +++ | – |
| H368 cells | +++ | – |
| H1335 cells | ++++ | – |
| A549 cells (erlotinib-resistant, dasatinib-partially resistant) | ++++ | – |
| H23 cells (erlotinib- and dasatinib-resistant) | +++ | – |

Note:
–: no CPE;
+++: CPE 50%-75%;
++++: CPE >75%

Biology of RSV NS1 Protein.

RSV genome contains individual genes for ten viral proteins [7]. The transcription of RSV genes is polar, with the promoter-proximal genes being transcribed more frequently than the promoter-distal ones. The NS1 gene is promoter-proximally located at the 3' end of the viral genome and therefore its mRNA is the most abundant of the RSV transcripts in a linear start-stop-restart mode [8] (FIG. 1). NS1 protein is referred to as nonstructural since it has not been detected in RSV particles. NS1 is exclusively found in RSV-infected cells. Our group, along with others, has found that NS1 can counter the type I IFN signaling during RSV infection [9, 10], implying that NS1 plays a direct role in inhibiting the host's innate immune response.

Mitochondria as Targets for Anticancer Agents.

Evasion from apoptotic cell death unregulated cell proliferation and eventual tumor development is one of the hallmarks of oncogenic cell transformation. We found that ΔNS1 RSV selectively induces apoptosis in tumor cells (FIG. 4), and also decreases mitochondrial ΔΨm and promotes mitochondrial swelling in A549 lung cancer cells, suggesting that mitochondrially-mediated apoptosis participates in the anti-tumor effect of ΔNS1 RSV.

RSV can be rendered nonpathogenic by mutating the NS1 gene so that it no longer inhibits IFN release, which attenuates viral infection in normal cells. However, these nonpathogenic RSV, ΔNS1 RSV, are still oncolytic because tumor cells are defective in their ability to produce and respond to IFN and, therefore, efficiently support the propagation of ΔNS1 RSV.

SUMMARY

This invention discloses a NS1 gene-deficient RSV (ΔNS1 RSV), which could be utilize to kill lung cancer cells, but not normal human cells. In one embodiment, the gene NS1 is deleted by the removal of 122 to 630 nt in the antigenomic cDNA using reverse genetics approach, resulting in the joining of the upstream nontranslated region of NS1 to the translational initiation codon of NS2. The ΔNS1 RSV was recovered through co-transfecting Vero cells with the NS1-deficient RSV cDNA and expressional plasmids encoding N, P, M2-1 and L. The RSV NS1 protein functions as a type-I-IFN antagonist, ΔNS1 RSV virotherapy produces more type-I-IFN, which prevents virus from replication in normal cells and also induces antitumor effects In another embodiment, the engineered virus could be any other virus having a similar strategy to delete NS1 gene, which functions as a gene encoding the related protein as a type-I-IFN antagonist.

In another embodiment, the ΔNS1 RSV can be applied to cancer spot by direct injection. Or the ΔNS1 RSV can be delivered to cancer spot through blood transfusion.

BRIEF DESCRIPTION OF THE FIGURES

FIG. 2 C-D. Subcutaneous A549 tumors were implanted in BALB/c nude mice and virotherapy is indicated by arrows below the x-axis. Control mice received equal volume of vehicle. Tumor sizes were measured at the end of treatment. Each data point represents a mean of 4 tumors measurements plus or minus the standard deviation.

FIG. 2 E-F. Tumors and organs were removed from the mice three days after injection of viruses. Homogenates of the tissue were prepared and assayed for viral titers and total RNAs were analyzed by RT-PCR for viral F gene expression [3]

Table 1. Cytopathic effect (CPE) test showing ANSI RSV selectively kills lung cancer cells

DETAILED DESCRIPTION OF THE INVENTION

The respiratory syncytial virus (RSV) was used in this study. The NS1 gene was deleted by the removal of 122 to 630 nt in the antigenomic cDNA using reverse genetics approach, resulting in the joining of the upstream nontranslated region of NS1 to the translational initiation codon of NS2. The ΔNS1 RSV was recovered through co-transfecting Vero cells with the NS1-deficient viral cDNA clone and expressional plasmids encoding N, P, M2-1 and L. Alternatively, the engineered virus could be any other viruses with the deletion of similar NS1 gene.

ΔNS1 RSV Preferentially Kills NSCLC Cells Both In Vitro and In Vivo.

Figure 1:
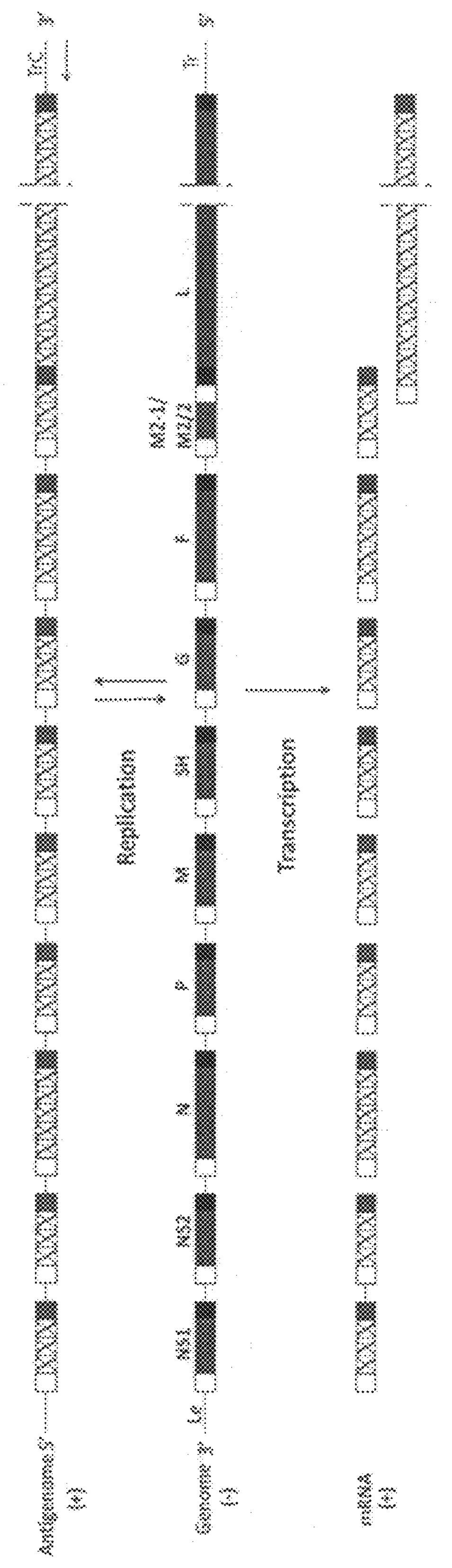
FIG. 1. Diagram of the RSV genome and its transcription and replication products. The virus genes are depicted as grey rectangles; the L gene, which comprises almost half of the genome, has been truncated. The GS and GE signals are shown as white and black boxes, respectively. The encoded anti-genome and mRNAs are indicated by hatched rectangles. Arrows indicate the location of the promoters.
Figure 2A:
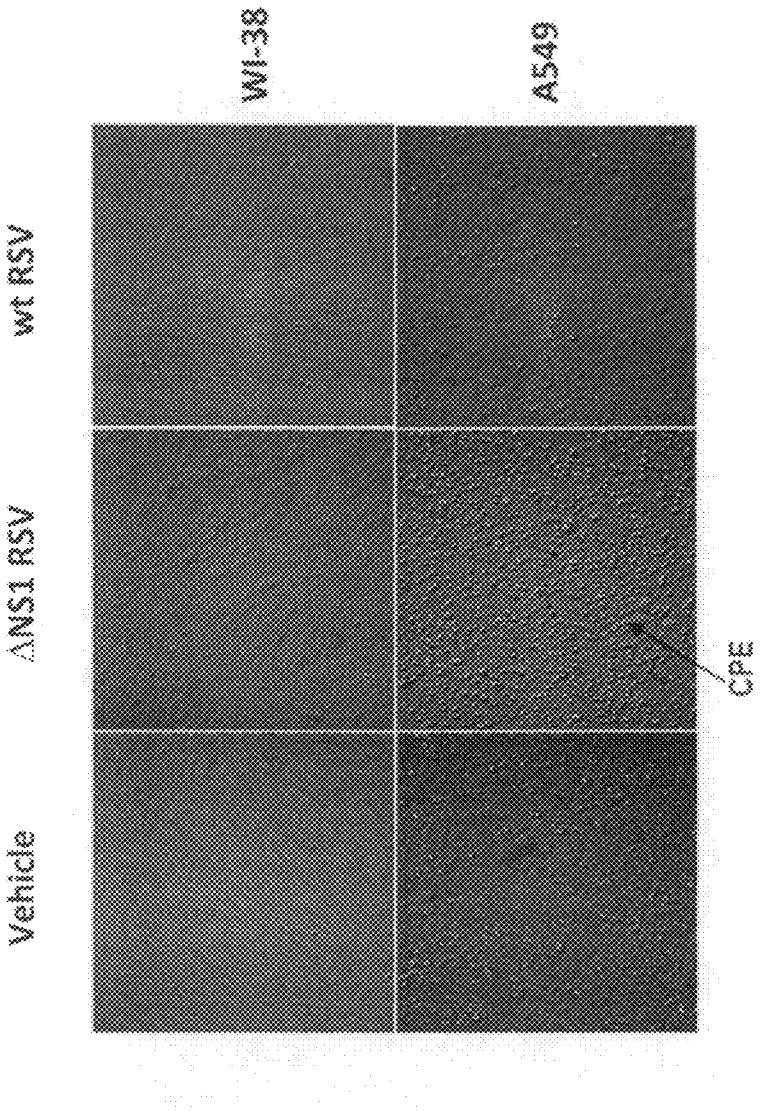
FIG. 2 A-B. Virus infection of NSCLC and normal cells. (A) Morphology of virus-infected A549 and WI-38 cells 24 h post-infection. (B) Viral titers as measured by plaque assay at 20 h after infection. Standard deviations from three independent experiments are shown by the error bars.
Figure 2B:
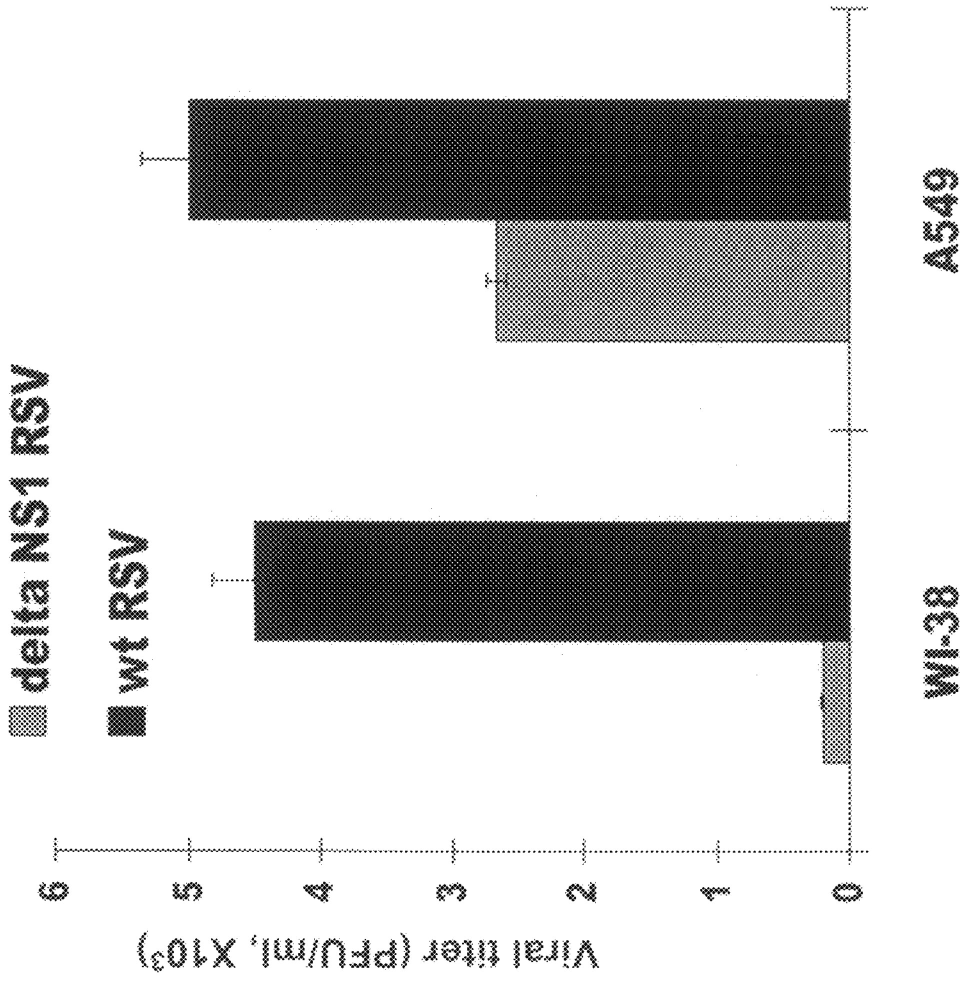

NSCLC cells and WI-38 normal human diploid lung cells were infected with wt or ΔNS1 RSV (MOI=5). Changes in cell morphology were observed and viral replication was measured. FIG. 2A shows that ΔNS1 RSV selectively induces CPE in A549 cells, and that ΔNS1 RSV has a higher viral titer in A549 cells than in WI-38 cells 24 hr after infection (FIG. 2B), suggesting that A549 cells efficiently support the propagation of ΔNS1 RSV because they are defective in producing and responding to IFN. Dr. Bose's group reported that wt RSV kills prostate cancer cells [11]. To test if the higher titer of wt RSV also kills lung tumor cells, we infected different lung tumor cell lines and normal WI-38 and NHBE cells with high dose of viruses (MOI=10), and checked CPE 24 hr post-infection. As shown in Table 1, ΔNS1 RSV, but not wt RSV, preferentially kills NSCLC cells. These experiments were done on cell lines in vitro, but proof of efficacy requires demonstration in vivo. To determine whether ΔNS1 RSV infection induces tumor growth regression in vivo, A549 cells were injected s.c. into the left and right flanks of 4-6 weeks old nude BALB/c mice (n=4 per group) and the resulting tumors were allowed to develop.

Figure 2C:
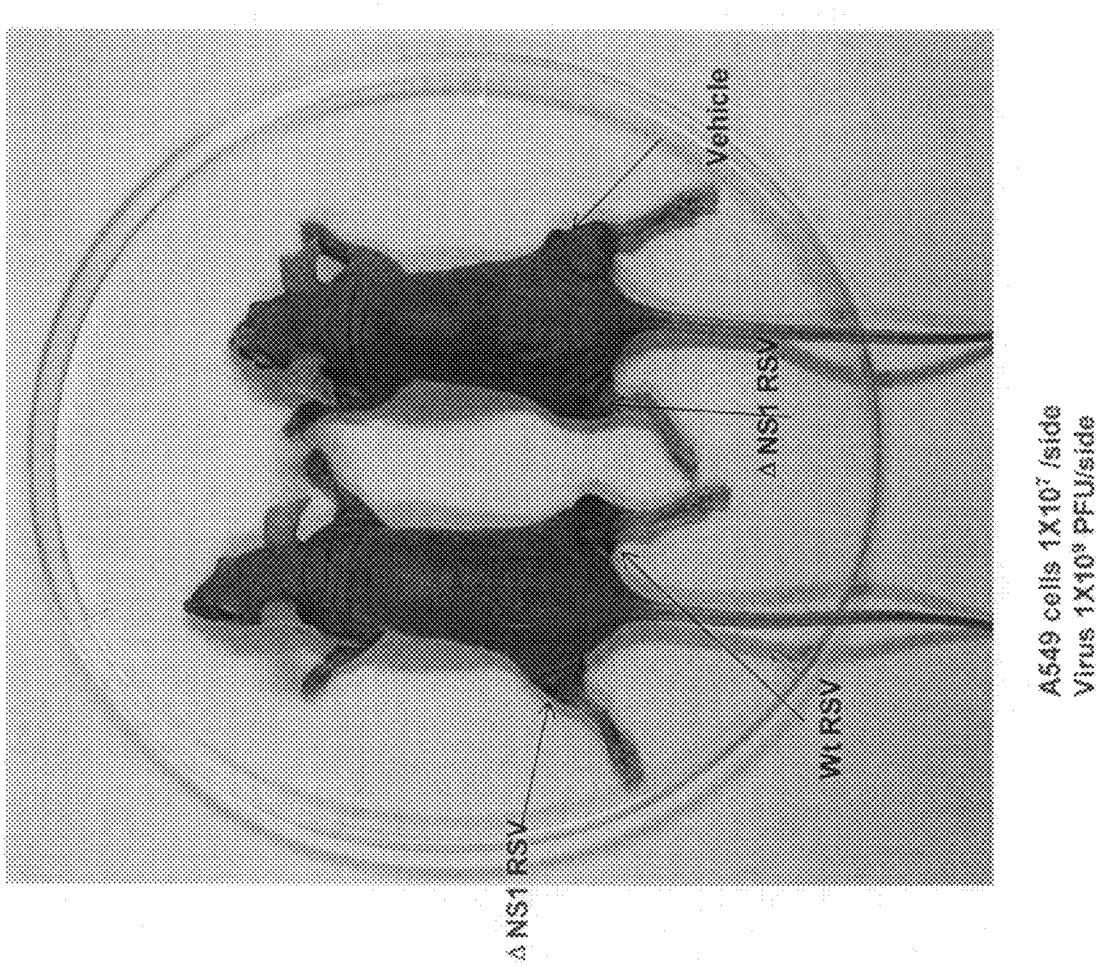
Figure 2D:
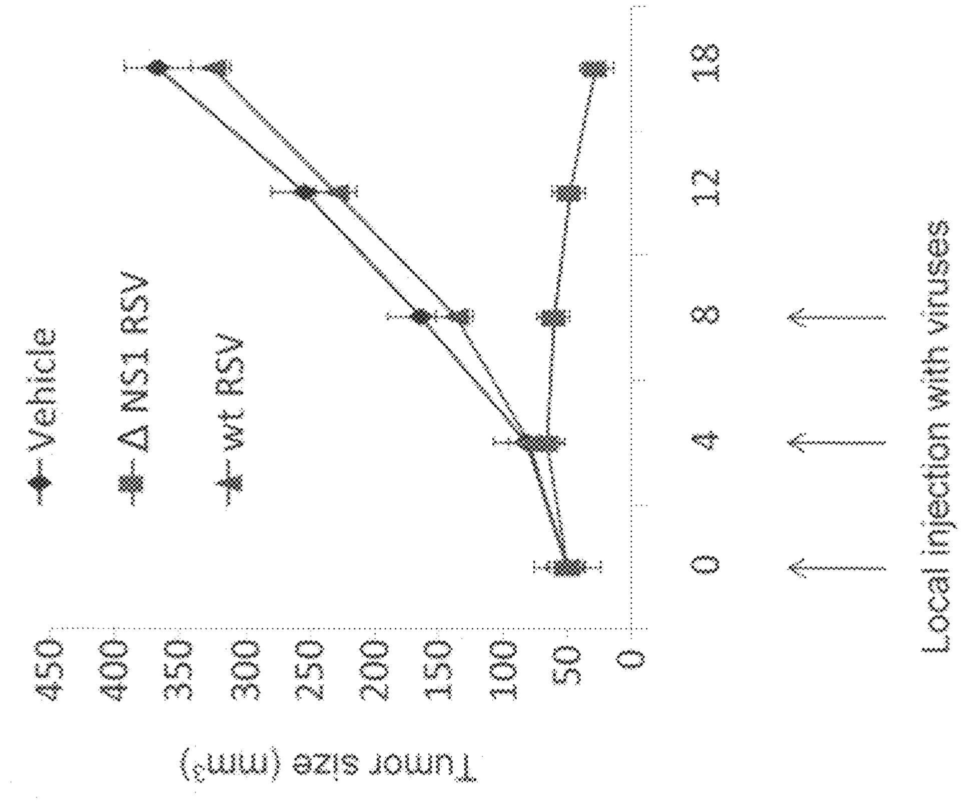

Viruses were locally injected into the tumors three times and the sizes of the tumors were measured using digital calipers. FIG. 2C, D show that ΔNS1 RSV infection caused regression in tumor growth versus controls. To test the safety of locally administered viruses, the virus titer in various organs of infected mice was determined by plaque assay and RT-PCR assay. As shown in FIG. 2E, F, the viruses specifically localize to tumors.

ΔNS1 RSV Induces Sub-G1 Peak in A549 Cells.

Figure 3:
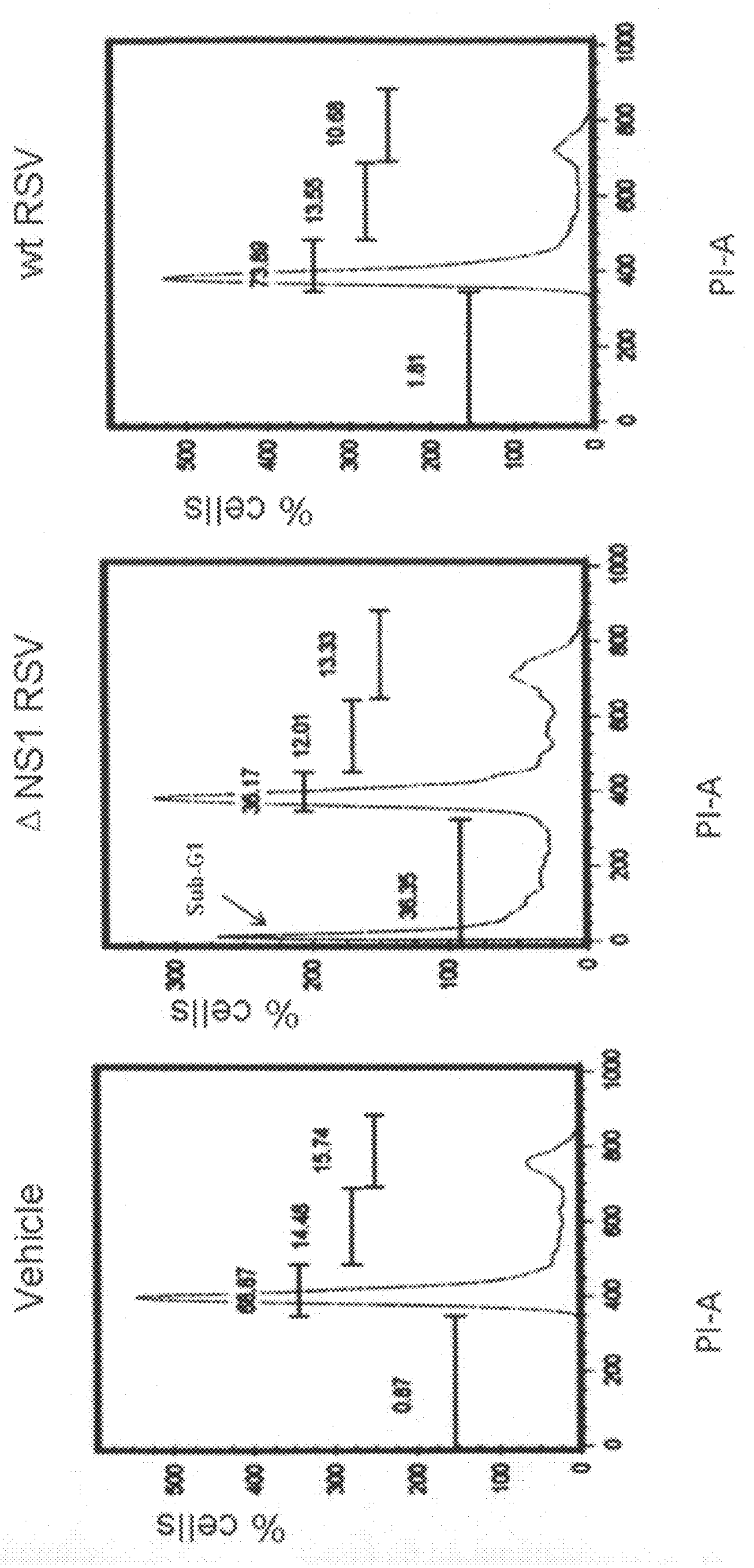
FIG. 3. Flow cytometric analysis of cell cycle. A549 cells were infected with indicated viruses (MOI=5), and 24 hr later the cells were collected and fixed with 70% cold aqueous ethanol. Cells were then stained with PI staining solution that contained propidium iodide (50 μg/ml; Sigma) and RNase A (50 μg/ml; Sigma) in the dark at room temperature for 30 min. Ten thousand cells were measured per sample, and the analysis was performed using the Cell Quest Pro software (Becton-Dickinson).

Cell cycle dysregulation is a critical feature of tumor cells. The inhibition of cell cycle is a potential therapeutic target for the control of tumor cell proliferation. To test whether ΔNS1 RSV induces cell cycle arrest, we infected A549 cells with the indicated viruses at an MOI of 5. Analysis of propidium iodide (PI) staining by flow cytometry clearly revealed that virus infection did not significantly affect tumor cell cycle, but the appearance of a sub-G1 (apoptosis) peak was considerably elevated in ΔNS1 RSV-infected cells (FIG. 3).

ΔNS1 RSV Infection Induces Apoptosis in Tumor Cells, but not in Normal Human Bronchial Epithelial Cells.

Figure 4A:
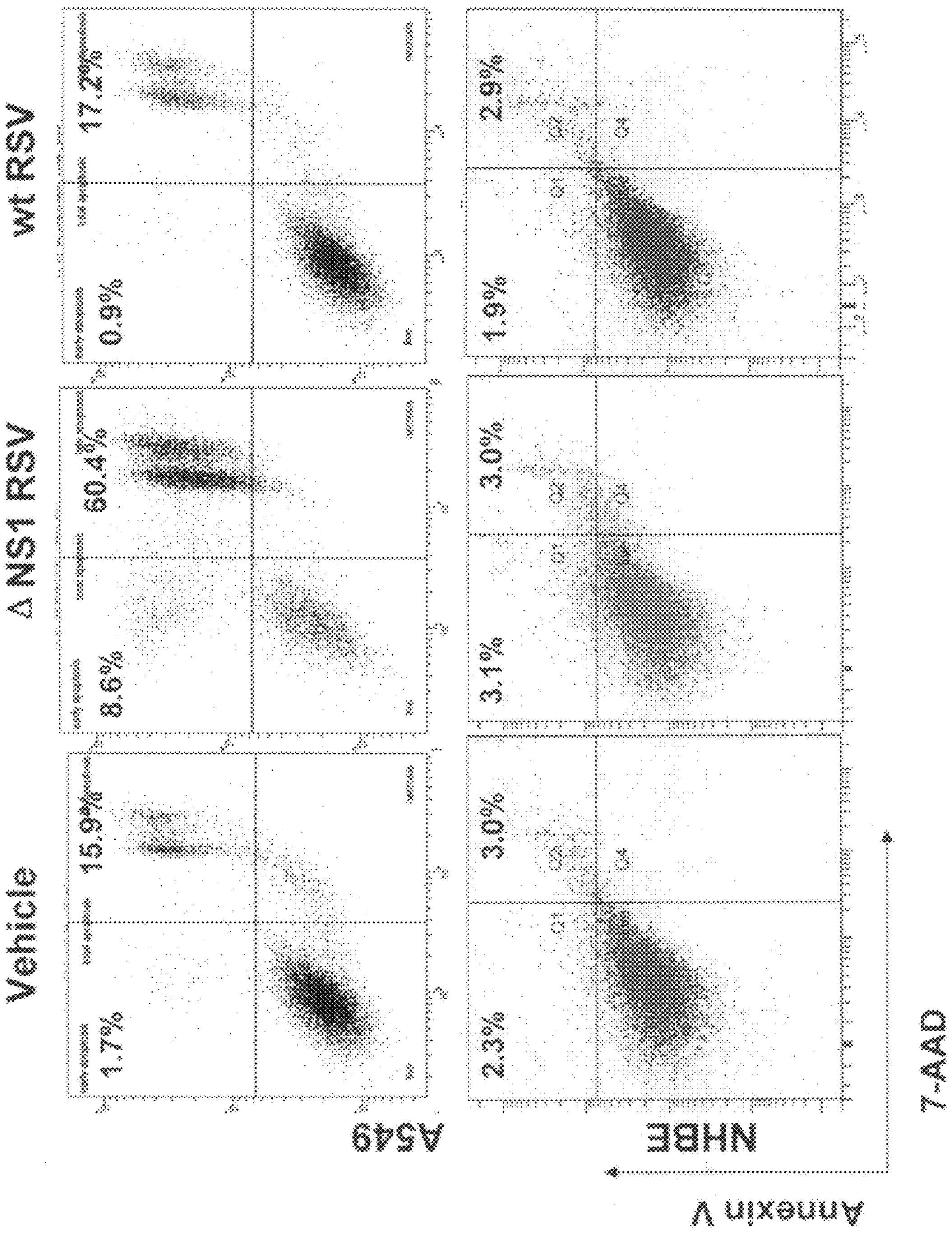
FIG. 4. NS1 protein prevents apoptosis and loss of mitochondrial ΔΨm. (A) A549 cells and NHBE cells were infected with indicated viruses (MOI=5), and collected at 20 and 48 hr post-infection for apoptosis analysis by annexin V-binding and PI uptake assay. (B-C) A549 cell were collected at 5 and 20 hr post-infection, and whole-cell lysates were immunoblotted. (D) H1299 (p53−/−) cells were treated and apoptosis was measured as described in (A).

To test the differential effect of ΔNS1 RSV infection on apoptosis, A549 cells and NHBE cells were infected with the indicated viruses (MOI=5) and apoptosis was measured by the annexin V binding assay. FIG. 4A shows that ΔNS1 RSV selectively induces apoptosis in tumor cells, compared to the cell spontaneous apoptosis shown in controls, which was verified by immunoblotting (FIG. 4B, C).

Recent research reports demonstrated that p53 participates in RSV-induced apoptosis [12]. To determine if p53 is required for ΔNS1 RSV-induced apoptosis, p53-deficient NSCLC H1299 were tested. FIG. 4D shows that ΔNS1 RSV infection induced apoptosis in H1299 cells, indicating that p53 protein is not an exclusive factor required for development of apoptosis in ΔNS1 RSV-infected tumor cells.

ΔNS1 RSV Infection Decreases Mitochondrial ΔΨm and Causes Mitochondrial Swelling.

Figure 4B:
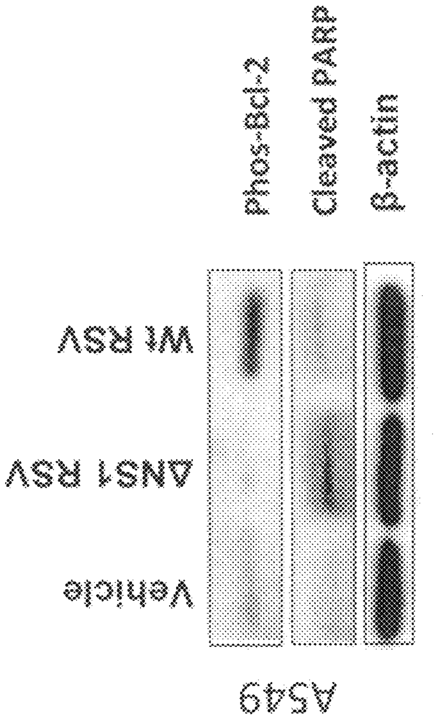
Figure 4C:
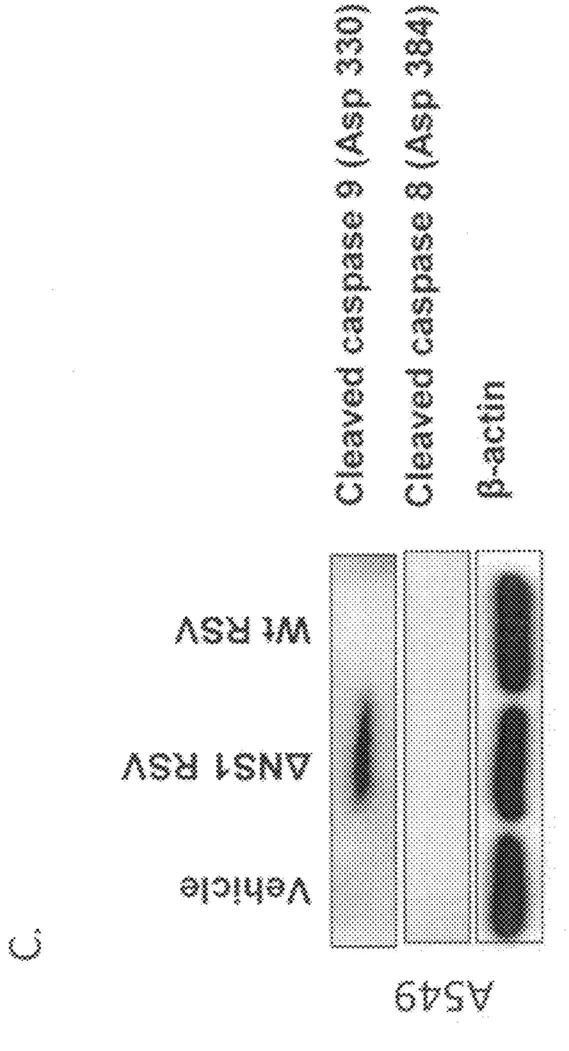
Figure 4D:
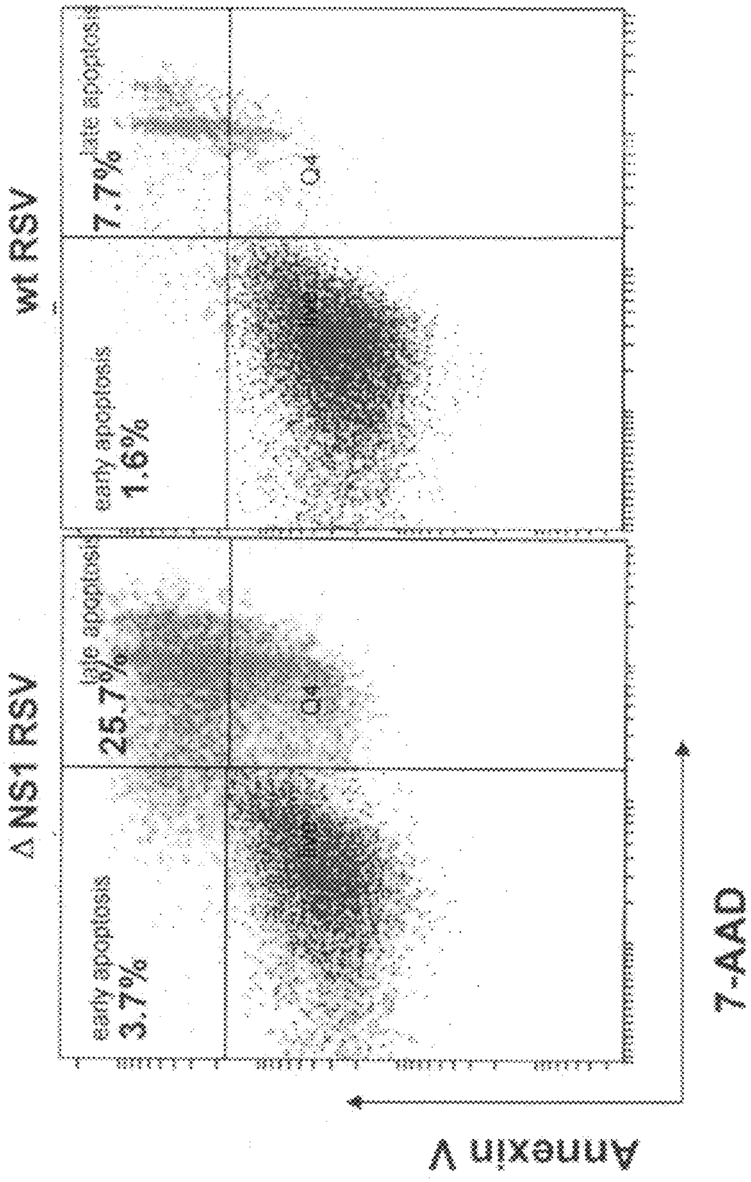
Figure 5C:
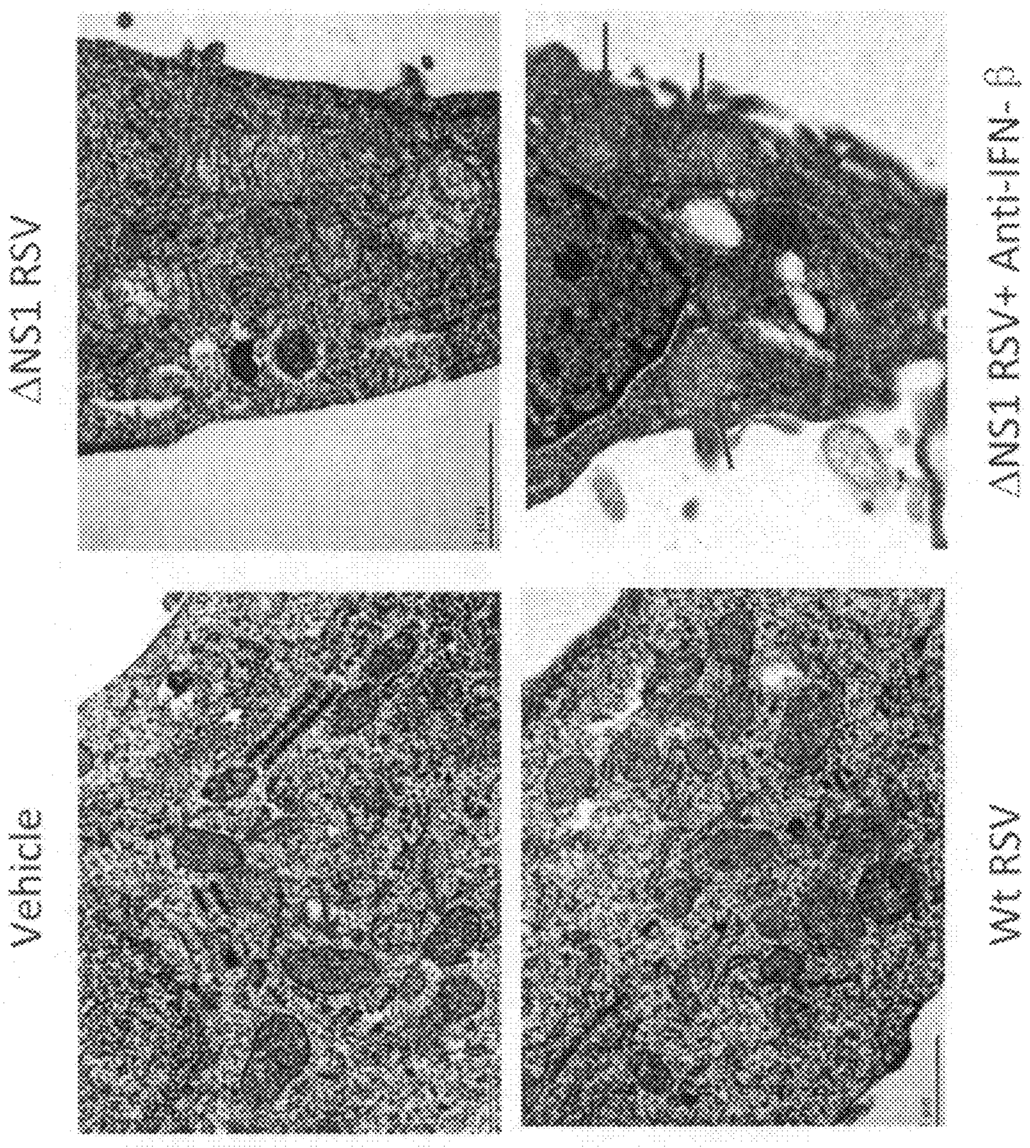
FIG. 5. ΔNS1 RSV infection decreases mitochondrial ΔΨm and induces mitochondrial ultrastructural alterations in A549 cells. (A-B) JC-1 dye was used to measure changes in mitochondrial ΔΨm by flow cytometry following viral infection. The red:green fluorescence intensity of JC-1 gives an index of the ΔΨm. P≤0.05 between wt and ΔNS1 RSV. (C) Transmission electron microscopy of mitochondrial morphology of virus-infected A549 cells is characterized by electron-dense matrix (arrows) and size of mitochondria.

We found that ΔNS1 RSV triggered apoptosis in lung cancer cells through mitochondrial pathway (FIG. 4B-C). To test the effects of viral infection on mitochondrial ΔΨm, we measured mitochondrial ΔΨm in A549 cells upon viral exposure (MOI=5). As shown in FIG. 5A, B, NS1 prevented loss of mitochondrial $\Delta\Psi m$ in response to viral infection. We further confirmed mitochondrial $\Delta\Psi m$ results by transmission electron microscopy. Mitochondria in vehicle-treated A549 cells exhibit a characteristic electron-dense matrix, in contrast to the swollen mitochondria with a loss of electron density in the matrix of ΔNS1 RSV-infected cells. Cells infected with wt RSV show less mitochondrial alteration than ΔNS1 RSV-infected cells. IFN-β did not significantly affect mitochondrial morphology upon ΔNS1 RSV infection (FIG. 5C).

REFERENCES

1. Molina, J. R., et al., *Non-small cell lung cancer: epidemiology, risk factors, treatment, and survivorship*. Mayo Clin Proc, 2008. 83(5): p. 584-94.
2. Jemal, A., et al., *Cancer statistics,* 2008. CA Cancer J Clin, 2008. 58(2): p. 71-96.
3. Bradley, J. D., et al., *Phase II trial of postoperative adjuvant paclitaxel/carboplatin and thoracic radiotherapy in resected stage II and IIIA non-small-cell lung cancer: promising long-term results of the Radiation Therapy Oncology Group—RTOG* 9705. J Clin Oncol, 2005. 23(15): p. 3480-7.
4. Xu, Q. Y., et al., *Identification of differential gene expression profiles of radioresistant lung cancer cell line established by fractionated ionizing radiation in vitro*. Chin Med J (Engl), 2008. 121(18): p. 1830-7.
5. Sekido, Y., K. M. Fong, and J. D. Minna, *Molecular genetics of lung cancer*. Annu Rev Med, 2003. 54: p. 73-87.
6. Spann, K. M., et al., *Suppression of the induction of alpha, beta, and lambda interferons by the NS*1 *and NS*2 *proteins of human respiratory syncytial virus in human epithelial cells and macrophages [corrected]*. J Virol, 2004. 78(8): p. 4363-9.
7. Collins, P. L., Y. T. Huang, and G. W. Wertz, *Identification of a tenth mRNA of respiratory syncytial virus and assignment of polypeptides to the* 10 *viral genes*. J Virol, 1984. 49(2): p. 572-8.
8. Tran, K. C., P. L. Collins, and M. N. Teng, *Effects of altering the transcription termination signals of respiratory syncytial virus on viral gene expression and growth in vitro and in vivo*. J Virol, 2004. 78(2): p. 692-9.
9. Zhang, W., et al., *Inhibition of respiratory syncytial virus infection with intranasal siRNA nanoparticles targeting the viral NS*1 *gene*. Nat Med, 2005. 11(1): p. 56-62.
10. Spann, K. M., et al., *Suppression of the induction of alpha, beta, and lambda interferons by the NS*1 *and NS*2 *proteins of human respiratory syncytial virus in human epithelial cells and macrophages [corrected]*. J Virol, 2004. 78(8): p. 4363-9.
11. Echchgadda, I., et al., *Anticancer oncolytic activity of respiratory syncytial virus*. Cancer Gene Ther, 2009.
12. Eckardt-Michel, J., et al., *The fusion protein of respiratory syncytial virus triggers p*53*-dependent apoptosis*. J Virol, 2008. 82(7): p. 3236-49.

The invention claimed is:

1. A method to treat lung cancer in a subject in need thereof, comprising 1) administering in a liquid medium to the neoplasm of a subject an engineered respiratory syncytial virus (RSV) with the NS1 gene deleted, wherein the RSV infects and causes oncolysis, thereby treating the neoplasm in the subject.

2. The method of claim 1 wherein the RSV further comprises viral NS2, N, M, SH, G, F, M2-1, P, and L genes.

3. A method to treat lung cancer in a subject in need thereof, comprising 1) administering to the neoplasm of a subject an engineered respiratory syncytial virus (RSV) with the NS1 gene deleted, wherein the RSV is suspended in saline, and wherein the RSV infects and causes oncolysis thereby treating the neoplasm in the subject.

* * * * *